(12) United States Patent
Franke et al.

(10) Patent No.: US 11,826,556 B2
(45) Date of Patent: Nov. 28, 2023

(54) INJECTOR DEVICE

(71) Applicant: SANOFI, Paris (FR)

(72) Inventors: Beate Franke, Frankfurt am Main (DE); Ulrich Brueggemann, Bridgewater, NJ (US); Jeff Kablik, Bridgewater, NJ (US)

(73) Assignee: Sanofi, Paris (FR)

( * ) Notice: Subject to any disclaimer, the term of this patent is extended or adjusted under 35 U.S.C. 154(b) by 520 days.

(21) Appl. No.: 16/968,954

(22) PCT Filed: Feb. 8, 2019

(86) PCT No.: PCT/EP2019/053084
§ 371 (c)(1),
(2) Date: Aug. 11, 2020

(87) PCT Pub. No.: WO2019/154959
PCT Pub. Date: Aug. 15, 2019

(65) Prior Publication Data
US 2020/0368451 A1  Nov. 26, 2020

(30) Foreign Application Priority Data
Feb. 12, 2018  (EP) ..................... 18305142

(51) Int. Cl.
*A61M 5/32* (2006.01)
*A61M 5/20* (2006.01)

(52) U.S. Cl.
CPC ........ *A61M 5/3257* (2013.01); *A61M 5/2033* (2013.01); *A61M 2005/2073* (2013.01)

(58) Field of Classification Search
CPC ............ A61M 5/31578; A61M 5/2033; A61M 5/3158; A61M 5/257; A61M 2005/2026;
(Continued)

(56) References Cited

U.S. PATENT DOCUMENTS 3,136,313 A  6/1964  Gosta et al.
5,709,668 A *  1/1998  Wacks ................ A61M 5/2033
                                                        222/326

(Continued)

FOREIGN PATENT DOCUMENTS

CH   279467   11/1951
CN   103118723   5/2013
(Continued)

OTHER PUBLICATIONS

PCT International Preliminary Report on Patentability in International Appln. No. PCT/EP2019/053084, dated Aug. 18, 2020, 8 pages.

(Continued)

*Primary Examiner* — Nathan R Price
*Assistant Examiner* — Sarah Dympna Grasmeder
(74) *Attorney, Agent, or Firm* — Fish & Richardson P.C.

(57) ABSTRACT

The present disclosure relates to an injector device comprising: a housing having a distal end and a proximal end; a medicament cartridge disposed within the housing; a needle unit comprising a needle, the needle unit being disposed in the distal end of the housing; and a button disposed in the proximal end of the housing, the button being configured to move the cartridge onto the needle unit to fluidly connect the needle with the cartridge when, in use, the button is pressed from an initial position into a depressed position.

17 Claims, 8 Drawing Sheets

(58) Field of Classification Search
CPC .... A61M 2005/2073; A61M 2005/206; A61M 2005/247; A61M 5/19; A61M 5/2248; A61M 5/3294; A61M 5/284; A61M 5/31596; A61M 5/326; A61M 5/347; A61M 5/50; A61M 5/5086; A61M 2005/1787; A61M 2005/3128; A61M 2005/3247; A61M 2005/3268; A61M 2005/2013

See application file for complete search history.

(56) References Cited

U.S. PATENT DOCUMENTS

| | | |
|---|---|---|
| 2006/0167412 A1 | 7/2006 | Marshall |
| 2013/0116625 A1 | 5/2013 | Holmqvist |
| 2016/0008540 A1 | 1/2016 | Fourt et al. |
| 2016/0106920 A1 | 4/2016 | Stefansen |
| 2016/0256630 A1* | 9/2016 | Kramer ............... A61M 5/5086 |
| 2017/0246403 A1* | 8/2017 | Cowe ................. A61M 5/2033 |
| 2017/0290986 A1* | 10/2017 | Chan .................. A61M 5/2466 |

FOREIGN PATENT DOCUMENTS

| | | | |
|---|---|---|---|
| CN | 103492001 | 1/2014 | |
| CN | 105025957 | 11/2015 | |
| CN | 107683153 | 2/2018 | |
| EP | 2489388 A1 * | 8/2012 | ............. A61M 5/20 |
| WO | WO 2012/022810 | 2/2012 | |
| WO | WO 2012/110583 | 8/2012 | |
| WO | WO 2014/159018 | 10/2014 | |
| WO | WO-2015185664 A1 * | 12/2015 | .......... A61M 5/2466 |
| WO | WO 2016/193346 | 12/2016 | |
| WO | WO 2016/193352 | 12/2016 | |

OTHER PUBLICATIONS

PCT International Search Report and Written Opinion in International Appln. No. PCT/EP2019/053084, dated Apr. 12, 2019, 12 pages.

* cited by examiner

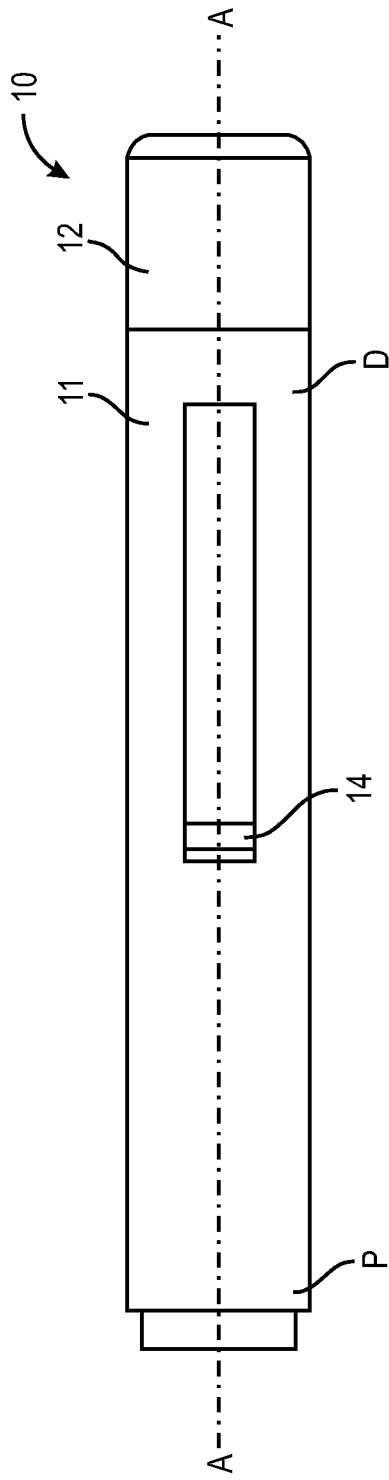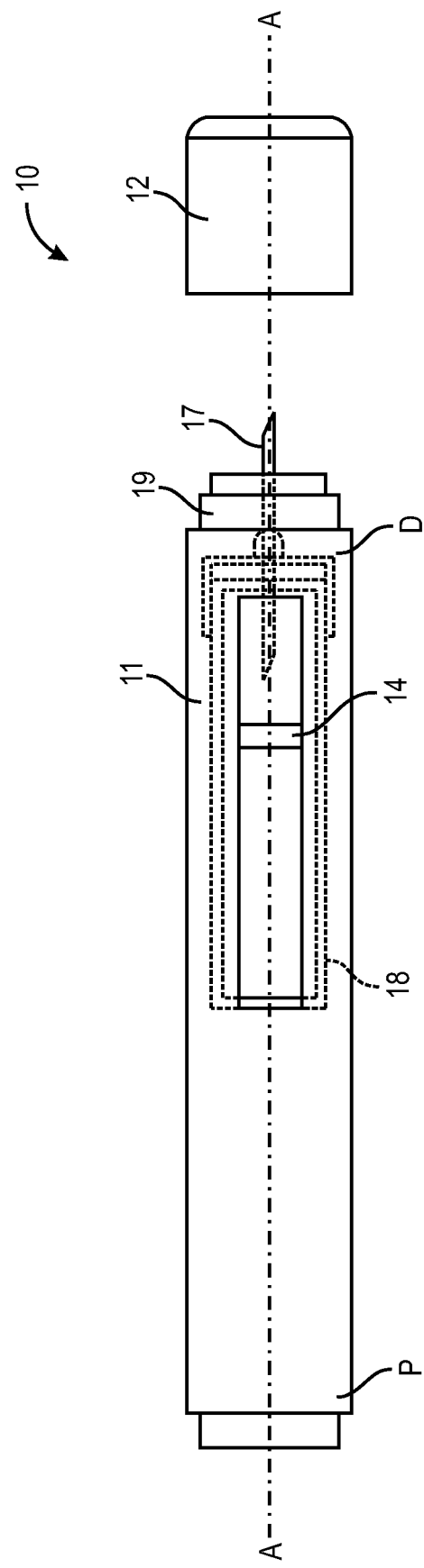
FIG. 1A
FIG. 1B

INJECTOR DEVICE

CROSS REFERENCE TO RELATED APPLICATIONS

The present application is the national stage entry of International Patent Application No. PCT/EP2019/053084, filed on Feb. 8, 2019, and claims priority to Application No. EP 18305142.4, filed on Feb. 12, 2018, the disclosures of which are incorporated herein by reference.

TECHNICAL FIELD

The present disclosure relates to an injector device for a medicament.

BACKGROUND

Cartridge injection devices, for example cartridge auto-injectors, typically have a sealed cartridge that contains a medicament, and a needle that is initially separated from the cartridge. An initial action moves the cartridge and needle together so that the needle pierces the cartridge. A plunger can then be moved into the cartridge to dispense medicament through the needle for injection to a user.

SUMMARY

It is an object of the present disclosure to provide an advantageous injector device having a housing having a distal end and a proximal end; a medicament cartridge disposed within the housing; a needle unit comprising a needle, the needle unit being disposed in the distal end of the housing; and a button disposed in the proximal end of the housing, the button being configured to directly act on the cartridge to move the cartridge onto the needle unit to fluidly connect the needle with the cartridge when, in use, the button is pressed from an initial position into a depressed position.

Therefore, prior to use of the device, the needle unit and needle are spaced from the cartridge. This has the advantage that the cartridge remains sealed up until the time that the device is required for use.

The device may further comprise a plunger displaceable to drive medicament from the cartridge through the needle; and a plunger mechanism triggerable to displace the plunger during operation of the device.

Therefore the plunger can be mechanically, rather than manually, operated to ensure consistent delivery characteristics.

The device may further comprise a sleeve displaceable along a longitudinal axis of the device between a first position in which the sleeve conceals the needle and a second position in which the needle is exposed from an end of the sleeve, the sleeve being configured to trigger the plunger mechanism when, during use, the sleeve is moved from the first position to the second position.

Therefore medicament is automatically delivered during injection.

The button may be configured to move the plunger mechanism and the cartridge simultaneously when, during operation of the device, the button is pressed from an initial position into a depressed position.

The sleeve may be axially spaced from the plunger mechanism when the button is in the first position, the button being configured to move the plunger mechanism into abutting relation with the sleeve when, during use, the button is pressed from the initial position to the depressed position.

Therefore the device is in an operable state when the button has been pressed.

The plunger mechanism may comprise a biasing member and a collar, the collar being rotatable about the longitudinal axis between a locked position, in which the biasing member is locked in place by the collar, and a unlocked position, in which the biasing member is free to displace the plunger; and wherein the sleeve is configured to rotate the collar when, during use, the sleeve is moved from the first position to the second position.

Therefore the plunger mechanism is simply operated so that medicament is automatically delivered during injection.

The sleeve may abut the collar when the button is in the depressed position.

Therefore the device is in an operable state when the button has been pressed.

The device may be further provided with a locking mechanism configured to prevent displacement of the sleeve when the button is in the initial position.

The locking mechanism prevents displacement of the sleeve and exposure of the needle before the device is in an operable state, that is to say, before the button is pressed by the user.

The locking mechanism may comprise a hook that depends from a wall of the device.

The hook may abut the sleeve to prevent the sleeve moving relative to the housing when the button is in the initial position.

The hook may abut the collar to prevent rotation of the collar when the button is in the initial position.

The button may be configured to act on the hook, when during use, it is moved from the initial position to the depressed position, to displace the hook out of abutting relation with the sleeve or collar.

When the button is in the initial position, a stop provided on the button may be spaced from an edge of the housing; and wherein a safety clip is provided which extends between the stop and the edge to prevent movement of the button so that, during use, the safety clip must be removed to enable the button to be pressed.

The button may be provided with a protrusion which extends through an L shaped slot in a wall of the device so that, when the button is in the initial position, the protrusion is located in a first portion of the L shaped slot which extends perpendicular to the longitudinal axis and prevents movement of the button from the initial position to the depressed position, the button being rotatable so that, in use, the button can be rotated to align the protrusion with a second portion of the slot extending parallel to the longitudinal axis and enable movement of the button into the depressed position.

Both the safety clip and the L shaped slot prevent accidental operation of the device.

The injector device may further comprise a reservoir of medicament in the medicament cartridge.

These and other aspects of the disclosure will be apparent from and elucidated with reference to the embodiments described hereinafter.

BRIEF DESCRIPTION OF FIGURES

Embodiments of the disclosure will now be described, by way of example only, with reference to the accompanying drawings, in which:

FIG. 1A is a schematic side view of an injector device and a removable cap;

FIG. 1B is a schematic side view of the injector device of FIG. 1A, with the cap removed from the housing;

DETAILED DESCRIPTION

Figure 2A:
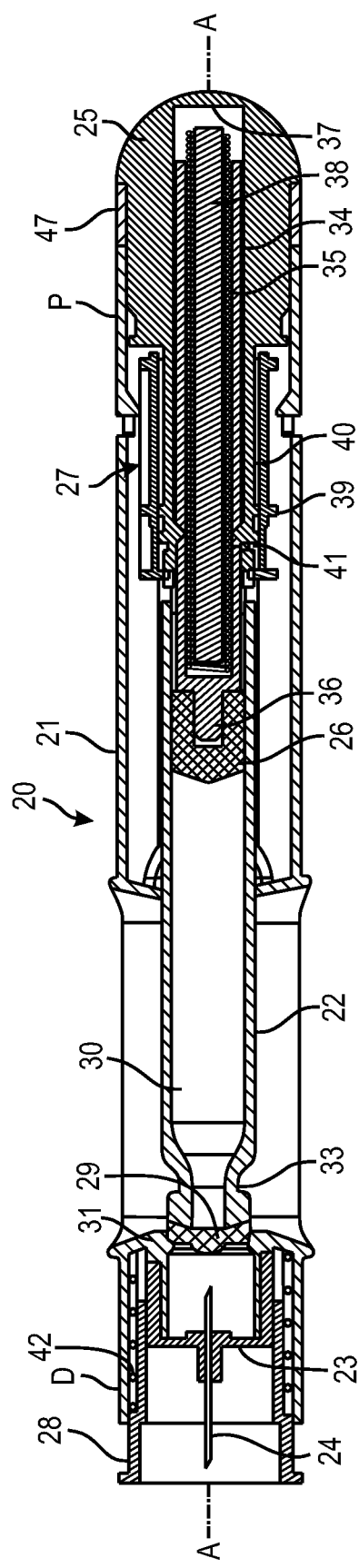
FIG. 2A shows a section view of an injector device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device may include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Injection is the process by which a stopper or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Figure 2B:
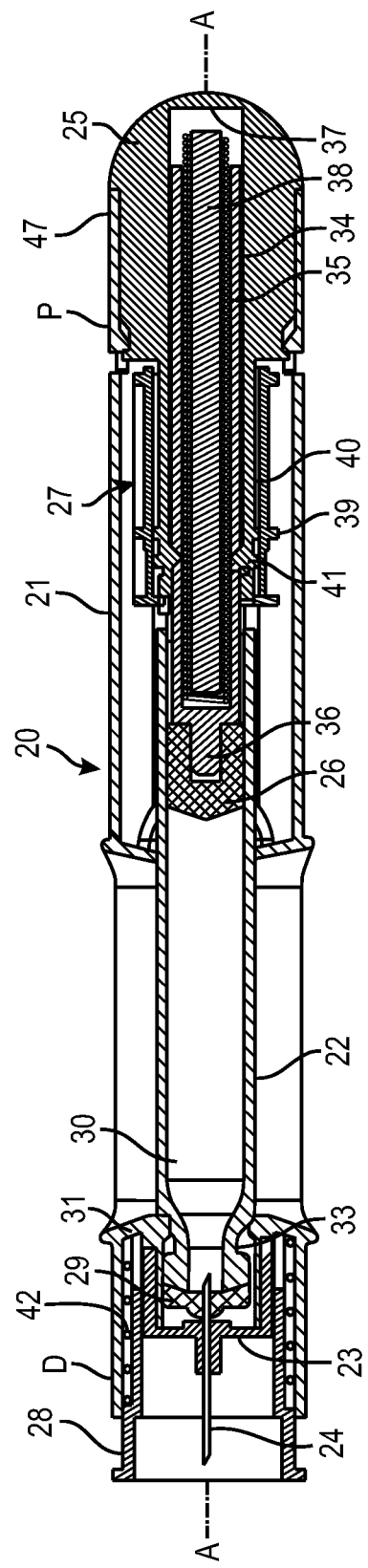
FIG. 2B shows a section view of the injector device of FIG. 2A with the button 25 in a depressed position.

FIG. 2A shows another injector device 20, the injector device 20 comprising: an elongate housing 21 having a distal end D and a proximal end P; a medicament cartridge 22 disposed within the housing 21; a needle unit 23 comprising a needle 24, the needle unit 23 being disposed in the distal end D of the housing 21; and a button 25 disposed in the proximal end P of the housing 21. The button 25 is configured to move the cartridge 22 onto the needle unit 23 to fluidly connect the needle 24 with the cartridge 22 when, in use, the button 25 is pressed from an initial position into a depressed position. FIG. 2B shows the button 25 in the depressed position.

The cartridge 22 has a distal end sealed by a foil cap or rubber bung 29, which is adjacent the needle unit 23, and a proximal end sealed by a plunger 26. A middle of the needle 24 is gripped by the needle unit 23, which itself is fixed in place relative to the housing 21 so that, during use, when the button 25 is depressed a proximal end of the needle 24 penetrates the foil or rubber seal 29 to communicate with a reservoir of medicament 30 provided in the cartridge 22. A restraint element 31 extends from an internal wall of the housing 21 adjacent the needle holder 23 to provide haptic feedback as the cartridge 22 engages the needle unit 23. In the illustrated example, the restraint element consists of a lip 31 which extends internally from the housing 21 toward the longitudinal axis A-A and into the path of the cartridge 22. The lip 31 has a degree resilient deformability so that when the user operates the button 25, the cartridge 22 pushes past the lip 31 which resists in a manner that is discernible to the user to signify that the cartridge 22 and the needle unit 23 have combined. With the button 25 in the depressed position, the lip 31 locates in a neck 33 of the cartridge to secure the cartridge 22 in the needle unit 23.

The device further comprises a plunger mechanism 27 triggerable to displace the plunger 26 during operation of the device 20 and drive medicament 30 from the cartridge 22. The plunger mechanism 27 is disposed between the button 25 and the cartridge 22 and comprises a shaft 34 which is mechanically coupled to the plunger 26. The shaft 34 is further coupled to a biasing member 35, in this case a coil spring which, when the plunger mechanism 27 is triggered, is displaced along the longitudinal axis A-A of the device to displace the plunger 26 and drive medicament 30 from the cartridge 22. In the illustrated example, the shaft 34 is hollow having a closed distal end 36 which abuts the plunger 26. The spring 35 is received in the hollow part of the shaft 34 with a distal end of the spring 35 abutted against the closed distal end 36 of the shaft 34 and proximal end abutted against an inside face 37 of the button 25. When the plunger mechanism 27 is triggered, the spring 35 is released from a coiled position and reacts against the inside face 37 of the button 25 and the closed end 36 of the shaft to displace the plunger 26. The mechanism 27 may further be provided with a pin 38 which locates within the coil spring 35 to stabilise the coil spring 35 and keep it aligned to the longitudinal axis A-A as it extends from the hollow portion of the shaft 34.

The illustrated plunger mechanism further comprises a collar 39, the collar 39 being rotatable about the longitudinal axis A-A between a locked position, in which the spring 35 is locked in place, and an unlocked position, in which the spring 35 is free to displace the plunger 26.

The collar 39 cooperates with locking arms 40 that hold the shaft 34 against the force of the spring 35, prior to operation of the device 20. The locking arms 40 are integral with the button 25 and extend therefrom into the housing 21. Ends of the arms 40 are provided with a protrusion 41 that each extend through a corresponding opening in the shaft 34 to prevent the shaft 34 moving in the axial direction independently of the button 25. In this way, the shaft 34 and plunger mechanism 27 are coupled to the button 25 when the collar is in the locked position.

The arms are inherently biased away from the shaft 34 but, with the collar 39 in the locked positon, are held against the shaft 34 by the collar 39. Rotation of the collar 39 into the unlocked position aligns slots in the collar 39 with each of the locking arms 40 so that they spring outwards through said slots and away from the longitudinal axis A-A. This action disengages the protrusions 41 from the holes in the shaft 34, thus allowing the spring 35 to displace the plunger 26.

Figure 3:
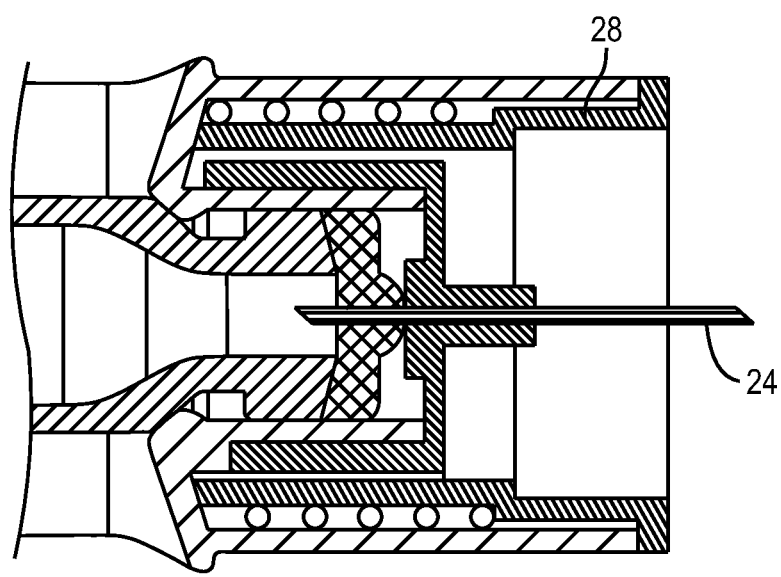
FIG. 3 shows a sleeve of the injector device in a second position.

The device is further provided with a sleeve 28 which is displaceable along the longitudinal axis A-A of the device 20 between a first position in which the sleeve 28 conceals the needle 24, as illustrated in FIG. 2, and a second position in which the needle 24 is exposed from an end of the sleeve 28, as shown in FIG. 3. The sleeve 28 is configured to trigger the plunger mechanism 27 when, during use, the sleeve 28 is moved from the first position to the second position.

The sleeve 28 slides telescopically with respect to the housing 21 and is biased into the first position by a spring 42. The spring 42 is disposed between the sleeve 28 and an inner surface of the housing 21 so that it is concealed during use of the device 20.

The plunger mechanism 27 is coupled to the button 25 by the locking arms, as described above, so that when the button 25 is depressed from the first position to the depressed position, the plunger mechanism 27 moves from an initial position, in which the plunger mechanism 27 is initially spaced from the sleeve 28, into a primed position in which the collar 39 of the plunger mechanism 27 abuts the sleeve 28.

Specifically, a follower surface of the collar 39 abuts a distal edge (not shown) of the sleeve 28, which distal edge is inclined relative to a direction perpendicular to the longitudinal axis A-A, so that, during axial displacement of the sleeve 28, the collar 39 is rotated by said inclined edge about the axis A-A from the locked position into the unlocked position.

During use, the button 25 is pressed into the depressed position to move the plunger mechanism 27 into the primed position and engage the needle unit 23 and cartridge 22; subsequently the distal end D of the device 20 is pressed up against an injection site of the user, displacing the needle shield 28 and causing the needle 24 to penetrate the user's skin, whereupon the displaced needle shield 28 triggers the plunger mechanism 27 and starts the injection event.

To prevent displacement of the sleeve 28 and exposure of the needle 24 before the device 20 is in an operable state—that is to say, before the button 25 is pressed by the user—the device 20 is further provided with a locking mechanism configured to prevent displacement of the sleeve 28 when the button 25 is in the initial position.

Figure 4:
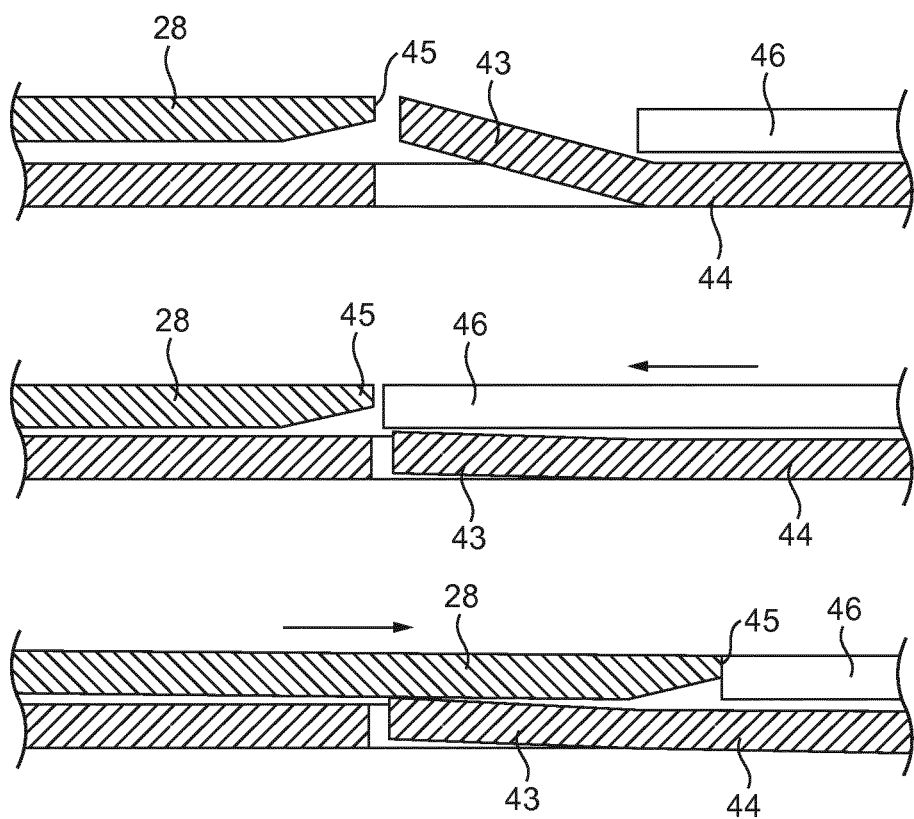
FIG. 4 shows a locking mechanism of the injector device.

In the example illustrated by FIG. 4, the locking mechanism may comprise a hook 43 that depends from a wall 44 of the device 20. In particular, the hook 43 may be a portion of wall 44 that is bent away from an inner face of the housing 21 toward the longitudinal axis A-A to obstruct the distal edge 45 of the sleeve 28. In such an example the button 25 will be provided with a releasing means 46. In the illustrated example the releasing means 46 is an arm which integrally formed with the button 25 and extends into the housing 21. The arm is configured to slide over the hook 43 to displace it outwards as the button 25 is moved from the first position to the depressed position, thereby allowing free movement of the sleeve 28.

In another unillustrated example, the hook may abut the collar 39 to prevent rotation of the collar 39 when the button 25 is in the initial position, thereby preventing the plunger mechanism 27 being triggered before the cartridge 22 has engaged the needle unit 23.

Figure 5:
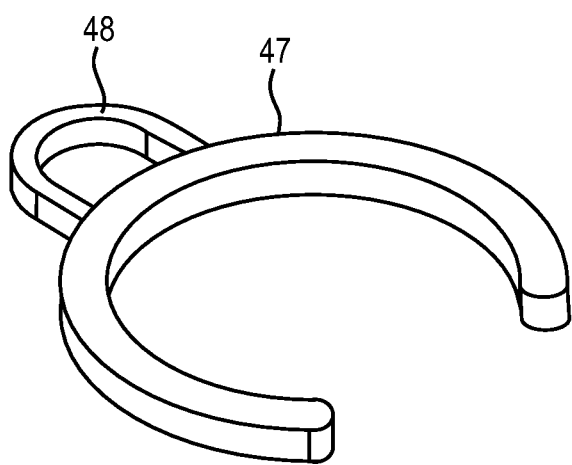
FIG. 5 shows a safety clip of the injector device.

As an additional safety feature, a safety clip 47, shown in FIGS. 2 and 5, may be provided. The safety clip 47 must be removed before the button 25 is pressed. In the illustrated example the safety clip 47 locates between a stop on the button and a proximal edge of the housing to prevent movement of the button 25 into the depressed position. In particular the button 25 has an elongate portion which is slideable against a proximal portion of the housing 21 to locate the button 25 as it moves between the initial and depressed positions. When the button 25 is in the initial position, the elongate portion is exposed from the proximal end P of the housing 21 and provides a surface about which the clip 47 may locate. So located, the clip abuts against both the proximal edge of the housing 21 and the stop to lock the button 25 in place. The clip is provided with a handle 48 which the user can grip to pull the clip 47 away from the device 20.

Figure 6:
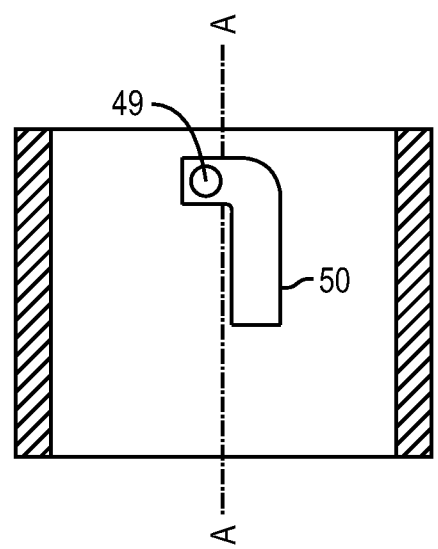
FIG. 6 shows a part of an injector device.

In another example illustrated in FIG. 6, the clip 47 is omitted and the elongate portion of the button 25 is provided with a protrusion 49 which extends through an L shaped slot 50 in a wall of the housing 21. Or alternatively, the L shaped slot 50 can be provided on the elongate portion of the button 25, with the protrusion 49 instead extending from the wall of the housing 21. In either case, when the button 25 is in the initial position, the protrusion 49 is located in a first portion of the L shaped slot 50 which extends perpendicular to the longitudinal axis A-A and prevents movement of the button 25 from the initial position to the depressed position, the button 25 being rotatable so that, in use, the button 25 can be rotated to align the protrusion 49 with a second portion of the slot 50 extending parallel to the longitudinal axis A-A and enable movement of the button 25 into the depressed position.

Figure 7:
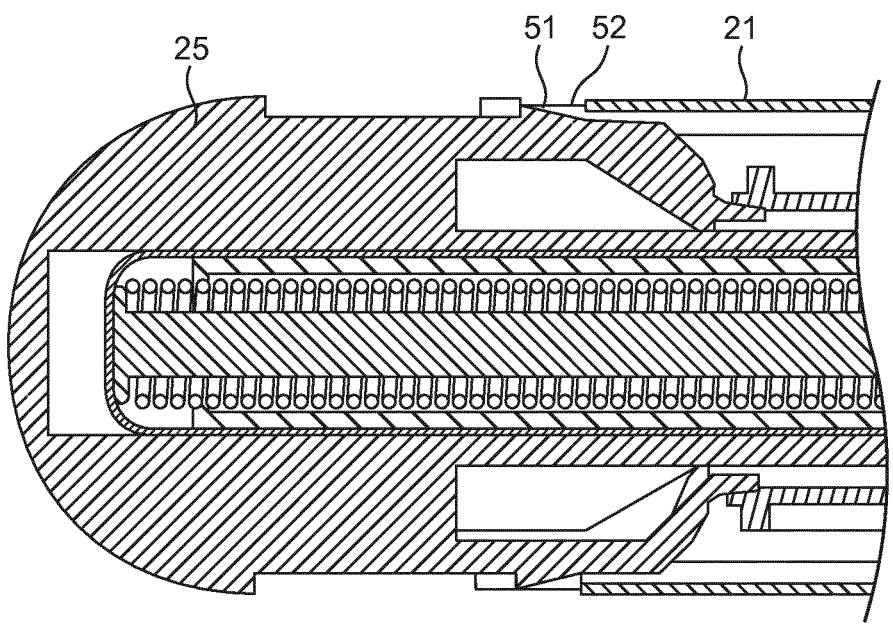
FIG. 7 is a detailed section view of a button of the injector device.

A rotated section of the button 25 is shown in FIG. 7. As shown, a barbed stop 51 is provided that cooperates with an opening 52 in the housing 21 to retain the button 25 in the housing 21. The barbed shape of the stop 51 allows movement of the button 25 in one direction only so that it can be pressed inwards but not pulled out of the housing 21. A second opening (not shown) in the housing 21 is provided which cooperates with the barbed stop 51 when the button 25 is in the depressed position. The second opening and the barbed stop 51 cooperate to react the force of the spring 35 against the inside face 37 of the button 25 when the collar 39 is in the unlocked position.

Figure 8:
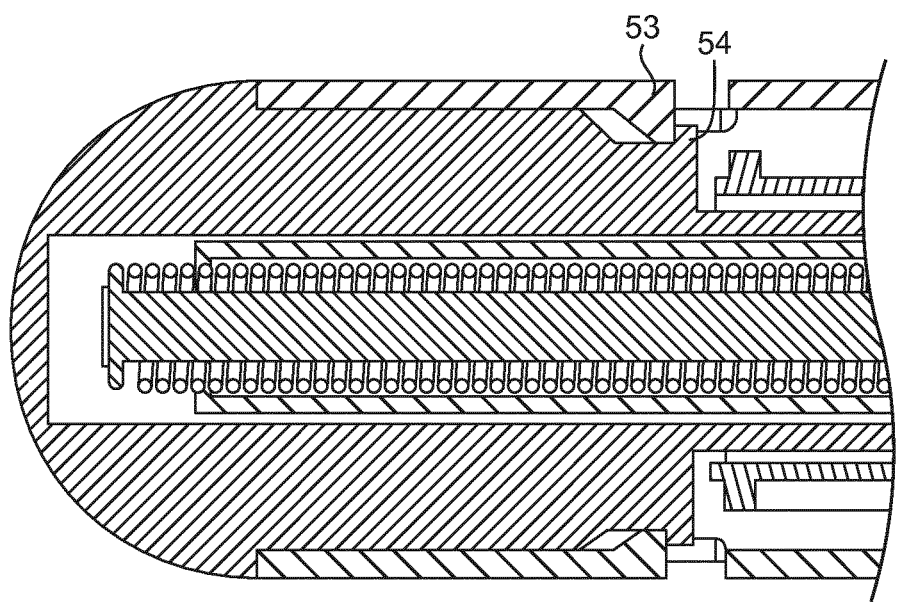
FIG. 8 is a detailed section view of the button of the injector device.

In another example shown in FIG. 8, an additional barbed stop 53 may depend from a wall of the housing 21 and engage with a distal edge 54 of the elongate portion of the button 25 when the button 25 is in the depressed position.

The injector device may further comprise a reservoir of medicament in the medicament cartridge.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful for the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. An auto-injector device comprising:
a housing having a distal end and a proximal end;
a medicament cartridge disposed within the housing;
a needle unit comprising a needle, the needle unit being disposed in the distal end of the housing;
a button disposed in the proximal end of the housing, the button being configured to directly act on the medicament cartridge to move the medicament cartridge onto the needle unit to fluidly connect the needle with the medicament cartridge when the button is pressed from an initial position into a depressed position during use
a plunger displaceable to drive a medicament from the medicament cartridge through the needle;
a plunger mechanism triggerable to displace the plunger during operation of the auto-injector device; and
a sleeve displaceable along a longitudinal axis of the auto-injector device between a first position relative to the housing in which the sleeve conceals the needle and a second position relative to the housing in which the needle is exposed from an end of the sleeve,
wherein the sleeve is configured to trigger the plunger mechanism in response to the sleeve being moved from the first position relative to the housing to the second position relative to the housing during use.

2. An auto-injector device according to claim 1, wherein the button is configured to move the plunger mechanism and the medicament cartridge simultaneously when the button is pressed from the initial position into the depressed position during operation of the auto-injector device.

3. An auto-injector device according to claim 2, wherein the sleeve is axially spaced from the plunger mechanism when the button is in the initial position.

4. An auto-injector device according to claim 1, wherein the plunger mechanism comprises a biasing member and a collar, the collar being rotatable about the longitudinal axis between a locked position, in which the biasing member is locked in place by the collar, and an unlocked position, in which the biasing member is free to displace the plunger; and wherein the sleeve is configured to rotate the collar when the sleeve is moved from the first position to the second position during use.

5. An auto-injector device according to claim 4, wherein the sleeve abuts the collar when the button is in the depressed position.

6. An auto-injector device according to claim 5, wherein the auto-injector device is further provided with a locking mechanism configured to prevent displacement of the sleeve when the button is in the initial position.

7. An auto-injector device according to claim 6, wherein the locking mechanism comprises a hook that depends from a wall of the auto-injector device.

8. An auto-injector device according to claim 7, wherein the hook abuts the sleeve to prevent the sleeve from moving relative to the housing when the button is in the initial position.

9. An auto-injector device according to claim 7, wherein the button is configured to act on the hook when the button is moved from the initial position to the depressed position during use to displace the hook out of an abutting relation with the sleeve or the collar.

10. An auto-injector device according to claim 1, wherein when the button is in the initial position, a stop provided on the button is spaced from an edge of the housing.

11. An auto-injector device according to claim 1, wherein the button is provided with a protrusion which extends through an L shaped slot in a wall of the auto-injector device.

12. An auto-injector device of according to claim 1, further comprising a reservoir of the medicament in the medicament cartridge.

13. An auto-injector device according to claim 3, wherein the button is configured to move the plunger mechanism into abutting relation with the sleeve when the button is pressed from the initial position to the depressed position during use.

14. An auto-injector device according to claim 10, wherein a safety clip is provided that extends between the stop and the edge of the housing to prevent movement of the button.

15. An auto-injector device according to claim 14, wherein the safety clip must be removed to enable the button to be pressed during use.

16. An auto-injector device according to claim 11, wherein when the button is in the initial position, the protrusion is located in a first portion of the L shaped slot that extends perpendicular to the longitudinal axis and prevents movement of the button from the initial position to the depressed position.

17. An auto-injector device according to claim 16, wherein the button is rotatable to align the protrusion with a second portion of the L shaped slot extending parallel to the longitudinal axis and to enable movement of the button into the depressed position.

* * * * *